(12) United States Patent
Dunn et al.

(10) Patent No.: US 8,545,841 B2
(45) Date of Patent: Oct. 1, 2013

(54) METHODS AND COMPOSITIONS FOR THE TREATMENT OF CANCERS AND PATHOGENIC INFECTIONS

(75) Inventors: William A. Dunn, Gainesville, FL (US); Debra E. Akin, Micanopy, FL (US); Ann Progulske-Fox, Gainesville, FL (US); David A. Ostrov, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 210 days.

(21) Appl. No.: 12/811,646

(22) PCT Filed: Jan. 5, 2009

(86) PCT No.: PCT/US2009/030102
§ 371 (c)(1),
(2), (4) Date: Jul. 2, 2010

(87) PCT Pub. No.: WO2009/089147
PCT Pub. Date: Jul. 16, 2009

(65) Prior Publication Data
US 2010/0285012 A1    Nov. 11, 2010

Related U.S. Application Data

(60) Provisional application No. 61/019,239, filed on Jan. 5, 2008.

(51) Int. Cl.
*A61K 39/00* (2006.01)
(52) U.S. Cl.
USPC ...................... 424/133.1; 424/145.1; 424/649
(58) Field of Classification Search
None
See application file for complete search history.

(56) References Cited

U.S. PATENT DOCUMENTS

2002/0165261 A1   11/2002  Borisy et al.
2005/0276809 A1   12/2005  Baehrecke et al.

FOREIGN PATENT DOCUMENTS

CA         2342470 A1 *  9/2002
WO    WO 2006/078774      7/2006
WO    WO 2007/051316      5/2007

OTHER PUBLICATIONS

Ardans, A, and G Walters. 1975. Efficacy studies with three formulations of cambendazole in horses. Am J Vet Res; 36(11): abstract.*
Holash, J, S Davis, N Papadopoulos, SD Croll, L Ho, M Russell, P Boland, R Leidich, D Hylton, E Burova, E Ioffe, T Huang, C Radziejewski, K Bailey, JP Fandl, T Daly, SJ Wiegand, GD Yancopoulos, and JS Rudge. 2002. VEGF-Trap: A VEGF blocker with potent antitumor effects. PNAS; 99(17): 11393-11398.*
Gozuacik, D. et al. "Autophagy as a cell death and tumor suppressor mechanism," *Oncogene*, 2004, pp. 2891-2906, vol. 23.

* cited by examiner

*Primary Examiner* — Carlos Azpuru
*Assistant Examiner* — David Browe
(74) *Attorney, Agent, or Firm* — Saliwanchik, Lloyd & Eisenschenk

(57) ABSTRACT

The subject application provides small compounds that are able to suppress autophagy in various cells. These compounds are useful in augmenting the existing treatments of various cancers and microbial/parasitic infections. Thus, the subject application also provides methods of treating various types of cancers and microbial/parasitic infections. Also provided by the subject application are methods of suppressing the expansion of autophagosomes within cells or individuals and inhibiting the lipidation of autophagy-related protein 8 (Atg8).

16 Claims, 7 Drawing Sheets

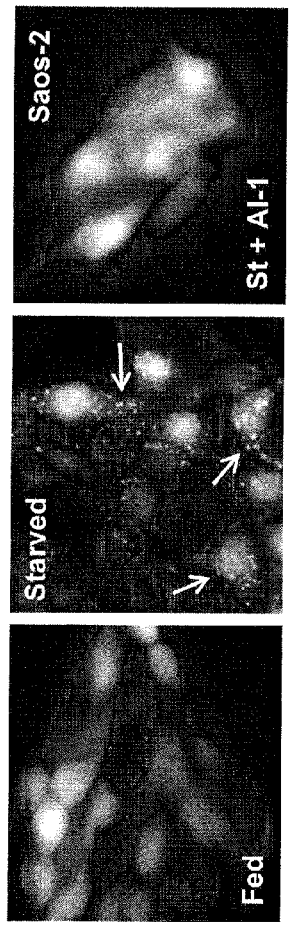
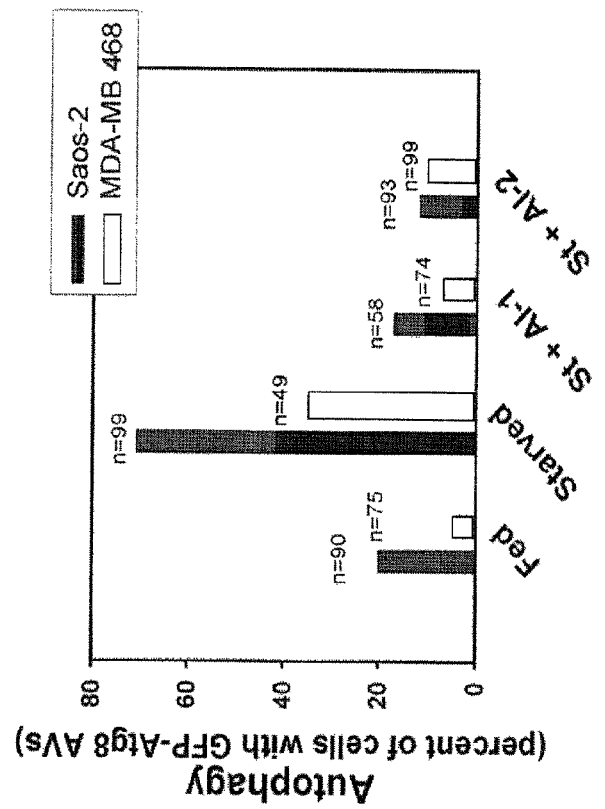

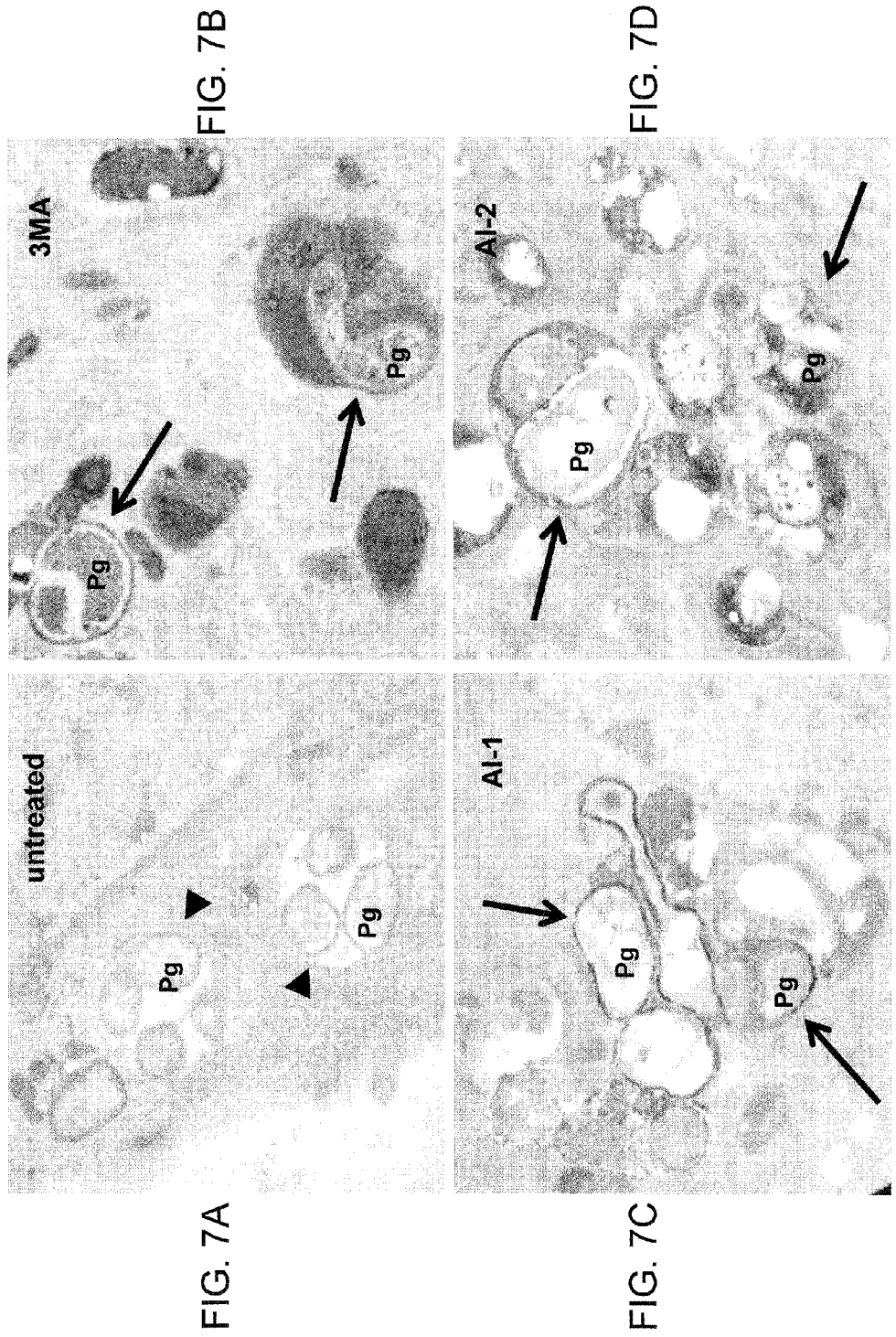

METHODS AND COMPOSITIONS FOR THE TREATMENT OF CANCERS AND PATHOGENIC INFECTIONS

CROSS-REFERENCE TO RELATED APPLICATION

This application is the U.S. national stage application of International Patent Application No, PCT/US2009/030102, filed Jan. 5, 2009, which claims the benefit of U.S. Provisional Application Ser. No. 61/019,239, filed Jan. 5, 2008, the disclosures of which are hereby incorporated by reference in their entirety, including all figures, tables and amino acid or nucleic acid sequences.

This invention was made with government support under 1 R01 CA095552 awarded by the National Institutes of Health. The government has certain rights in the invention.

BACKGROUND OF THE INVENTION

Many bacteria have evolved mechanisms to invade eukaryotic cells and survive intracellularly. After cell invasion, bacteria use a variety of mechanisms to evade degradation. Initially, bacteria are sequestered into an endosome-like vacuole. Some pathogens, such as *Actinobacillus actinomycetemcomitans, Listeria monocytogenes, Rickettsia* and *Shigella*, lyse the vacuole and enter the cytoplasm. However, some intracellular pathogens reside within vacuoles that mature through the endocytic pathway and are modified to prevent lysosomal fusion and acquisition of hydrolytic enzymes. A third group of bacteria that includes *Brucella abortus, Legionella pneumophila* and *Porphyromonas gingivalis* infiltrate the autophagic pathway during their intracellular life cycle.

Autophagy is an essential cellular pathway for the degradation of macromolecules and recycling of anabolic precursors such as amino acids. This pathway is useful in the removal of protein aggregates present in a number of neurological disorders and is essential for the survival of breast carcinoma (e.g., MDA-MB468 and MDA-MB231), osteosarcoma (Saos-2), and hepatoma (HuH7) cell lines when deprived of amino acids and serum growth factors.

BRIEF DESCRIPTION OF THE FIGURES

FIGS. 2A-2D. Atg-4-targeted drugs decreased the number of Atg8 (LC3)-labeled autophagic vacuoles. Saos-2 osteosarcoma and MDA-MB468 breast carcinoma cells stably expressing GFP-Atg8 were incubated under nutrient fed and starved (St) conditions in the presence and absence of AI-1 and AI-2. The presence GFP-Atg8 labeled autophagic vacuoles appear as dots (arrows) in starved Saos-2 cells (FIG. 2B). Atg8-labeled vacuoles are not observed in fed Saos-2 cells or starved cell treated with AI-1. Almost 70% of the starved cells contained autophagic vacuoles. However, the number of starved cells containing autophagic vacuoles was dramatically reduce upon treatment with AI-1 and AI-2 (FIG. 2D; n=number of cells counted).

FIG. 5B) conditions in the presence and absence of AI-1 (FIG. 5C) and AI-2 (FIG. 5D), Autophagic vacuoles (arrows) were visualized by electron microscopy. The "black" reaction product of CMPase, a lysosomal enzyme, can be seen within small lysosomes, many larger autophagic vacuoles (arrows) as well as the Golgi apparatus (Go).

FIGS. 7A-7D. The inhibition of autophagy by AI-1 and AI-2 results in the trafficking of *P. gingivalis* to lysosomes. Human coronary arterial endothelial cells (HCAEC) were exposed to *P. gingivalis* (Pg) in the absence (FIG. 7A) and presence of 3-methyladenine (3MA) (FIG. 7B) and compounds AI-1 (FIG. 7C) and AI-2 (FIG. 7D). In untreated cells, *P. gingivalis* was observed in replicating vacuoles lacking the lysosomal enzyme CMPase (arrowheads). In cells treated with 3MA, AI-1, or AI-2, the partially degraded bacteria were found in CMPase-positive lysosomes (arrows).

DETAILED DISCLOSURE OF THE INVENTION

This application provides compositions and methods for improving the therapeutic efficacy of various cancer treatments, for example endocrine therapy, chemotherapy or radiation therapy, by inhibiting the cellular process of macroautophagy, also referred to commonly as autophagy. Inhibition of Atg4, as provided by the subject invention, can increase the therapeutic efficacy of regimens commonly employed to treat cancer, such as for example, endocrine therapy, chemotherapy or radiation therapy.

Figure 1:
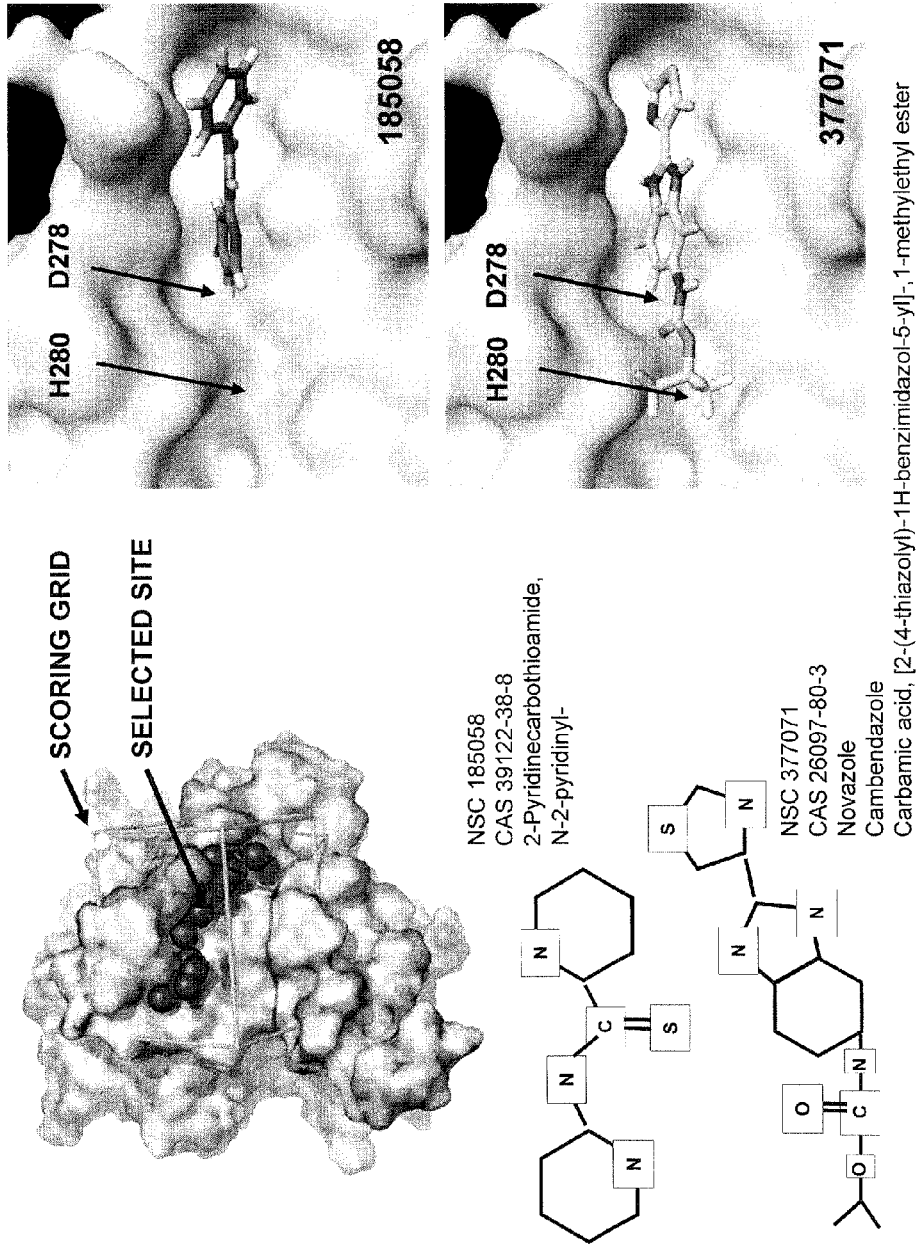
FIG. 1. In silica molecular docking of small compounds into the active site of Atg4 (autophagy-related protein 4. Compounds AI-1 (NSC 185058; CAS 39122-38-8) and AI-2 (NSC 377071; CAS 26097-80-3) are illustrated in FIG. 1.

Another aspect provides compounds and compositions suitable for reducing or inhibiting the cytoprotective autophagic response of cancer cells to certain therapies, for example cancer therapies. Thus, the subject application provides approaches to reducing or inhibiting Atg4 function in cells, thus reducing or eliminating the cells ability to engage a protective autophagic response, either concurrent to or after therapy. Thus, the methods provided in this application also provide for improving the efficacy of a cancer therapy, including endocrine therapeutic, chemotherapeutic or radiation treatments comprising the administration of compounds disclosed herein to a patient having cancer. In certain aspects of the invention, compounds such as N-2-pyridinyl-2-pyridinecarbothioamide and/or cambendazole can be used in the practice of the invention (see, for example, compounds AI-1 (NSC 185058; CAS 39122-38-8) and AI-2 (NSC 377071; CAS 26097-80-3) as illustrated in FIG. 1).

In the context of the subject application, the phrase "increasing the cellular response" refers to increasing the rate at which, or the degree to which, a cell responds to the cancer therapy, increasing or augmenting the effect of a cancer therapy on a cell, or increasing the likelihood that a cell will respond to the cancer therapy, as compared with the cellular response to the cancer therapy alone in the absence of the administration of compounds and compositions as disclosed herein.

The term "cell" refers to a single cell, a plurality of cells or a population of cells, unless otherwise indicated herein. The cell can be a cancerous cell, a cell that is suspected of being cancerous or pre-cancerous, or a cell that is pre-disposed to becoming cancerous or pre-cancerous. The cell may be a transformed cell or a cell undergoing abnormal or uncontrolled growth. The cell may be a cancerous cell with stem-cell like properties or a stem-cell with cancerous properties, for example uncontrolled proliferation or the capacity to differentiate into other cell types. However, in those embodiments in which bacterial or parasitic infections are being treated, the cell is, typically, not cancerous or malignant. The cell may be a cell in culture or it may be a cell within a subject. The cell may be derived from any organism whose cells undergo autophagy, and in particular embodiments is a mammalian cell, including a mouse cell, a rat cell, a rabbit cell or a human cell.

A cell that is currently undergoing cancer therapy refers to a cell that is currently being treated with a cancer therapy regimen, including simultaneously with, overlapping with, or sequentially prior to or following the administration of compounds or compositions that inhibit Atg4. In various aspects of the invention, the cancer therapy may be any one of a number of therapies given to a cell to treat, inhibit or prevent cancer and may, for example, include one or more therapies (e.g., chemotherapy, endocrine therapy, radiation therapy and/or chemoradiation therapy). Chemotherapy refers to treatment with drugs or chemical compounds that target cancer cells. Endocrine therapy, also called hormone therapy, refers to treatment that removes, blocks, or adds hormones. Radiation therapy refers to the use of high-energy radiation from x-rays, gamma rays, neutrons, protons and other sources to target cancer cells. Radiation may be administered externally or it may be administered using radioactive material given internally. Chemoradiation therapy combines chemotherapy and radiation therapy. In some aspects of the invention, the cancer therapy may have a cytotoxic or cytostatic effect. The cancer therapy may also be a therapy that invokes or induces cytoprotective autophagy in the cell.

The chemotherapy or endocrine therapy may involve, without limitation, administration of a chemotherapeutic agent or endocrine therapeutic agent comprising a small molecule, a peptide or a protein, an anthracycline, an alkylating agent, an alkyl sulfonate, an aziridine, an angiogenesis inhibitor, an ethylenimine, a methylmelamine, a nitrogen mustard, a nitrosourea, an antibiotic, an antimetabolite, a folic acid analogue, a purine analogue, a pyrimidine analogue, an enzyme, a podophyllotoxin, a platinum-containing agent or a cytokine. Preferably, the chemotherapeutic agent or endocrine therapeutic agent is one that is known to be effective against the particular cancer and cell type. Exemplary chemotherapeutic agents include taxanes, tamoxifen, cisplatin, adriamycin (ADR), 5-fluorouracil (5-FU), etoposide, doxorubicin, VEGF-TRAP and variants thereof (see, for example, *Proc. Natl. Acad. Sci.,* 2002, 99:11393-11398), AdPEDF (Adenovector Pigment Epithelium-Derived Factor; *Retina, The Journal Of Retinal And Vitreous Diseases,* 2005, 25(No. 8):S48) small molecule tyrosine kinase inhibitors that target VEGFRs (such as cediranib (4-[(4-fluoro-2-methyl-1H-indol-5-yl) oxy]-6-methoxy-7-[3-(pyrrolidin-1-yl)propoxy] quinazoline), sunitinib (N-[2-(diethylamino)ethyl]-5-[(Z)-(5-fluoro-1,2-dihydro-2-oxo-3H-indol-3-ylidine)methyl]-2, 4-dimethyl-1H-pyrrole-3-carboxamide), sorafenib (4-[4-[[4-chloro-3-(trifluoromethyl)phenyl]carbamoylamino] phenoxy]-N-methyl-pyridine-2-carboxamide) or pazopanib (benzenesulfonamide, 5-[4-[(2,3-dimethyl-2H-indazol-6-yl) methylamino]-2-pyrimidinyl]-amino]-2-methyl-monohydrochloride)), thalidomide (2-(2,6-dioxopiperidin-3-yl) isoindoline-1,3-dione), lenalidomide (REVLIMID; 3-(4-amino-1-oxo-3H-isoindol-2-yl)piperidine-2,6-dione)), bevacizumab, HERCEPTIN (trastuzumab), or camptothecin.

The phrase "treating cancer" refers to an approach for obtaining beneficial or desired results, including clinical results. Beneficial or desired clinical results can include, but are not limited to, alleviation or amelioration of one or more symptoms or conditions, diminishment of extent of disease, stabilization of the state of disease, prevention of development of disease, prevention of spread of disease, delay or slowing of disease progression, delay or slowing of disease onset, amelioration or palliation of the disease state, and remission (whether partial or total). Treating can also mean prolonging survival of a subject beyond that expected in the absence of treatment. In certain embodiments, cancers that are to be treated include, but are not limited to, breast cancer, pancreatic cancer, prostate cancer, gynecological cancers (e.g., ovarian cancer or cervical carcinoma), skin cancer (e.g., melanoma), brain cancer, neuroblastoma, glioma, a solid tumor, a hematologic malignancy (e.g., leukemia or lymphoma), head and cancer, ganglioneuroma, infiltrating ductal carcinoma of the breast, adenocarcinoma of the lung, pancreatic adenocarcinoma, pancreatic islet cell tumor, liver cancer, gastric cancer, bladder cancer, colon cancer, prostate cancer, lung cancer or nasopharyngeal carcinoma. Treating can also mean inhibiting the progression of disease, slowing the progression of disease temporarily, or halting the progression of the disease permanently. Additionally, individuals suitable for treatment as set forth herein can be a mammal, including humans, cats, dogs, horses, mice or rats.

In various aspects of the invention, compositions disclosed herein can be used in combination with a given cancer therapy and an effective amount of a composition as disclosed herein is administered to an individual. The term "effective amount" means an amount effective, at dosages and for periods of time necessary to achieve the desired result, for example, the inhibition of Atg4 within the individual. Compositions containing the compounds disclosed herein may be administered to a subject using a variety of techniques. For example, the agent may be administered systemically, which includes by injection including intramuscularly or intravenously, orally, sublingually, transdermally, intraarterially, subcutaneously or internasally. Alternatively, the compositions may be administered directly at a site at which the cancer is located. Delivery to the site includes topical administration, injection to the site, or surgical implantation, for example at a site of a tumor.

Other embodiments of the subject invention provide for compositions comprising chemotherapeutic agents and the compounds disclosed herein for administration to an individual with cancer. Regardless of whether the compounds disclosed herein are administered alone or in combination with a chemotherapeutic agent, a pharmaceutically acceptable diluent can be used. The proportion and identity of the pharmaceutically acceptable diluent may be determined by the chosen route of administration, compatibility with live cells, and standard pharmaceutical practice. Generally, the pharmaceutical composition will be formulated with components that will not significantly impair the biological properties of the compounds disclosed herein.

The pharmaceutical composition can be prepared by methods for the preparation of pharmaceutically acceptable compositions suitable for administration to patients Suitable vehicles are described, for example, in Remington's Pharmaceutical Sciences (Remington's Pharmaceutical Sciences, Mack Publishing Company, Easton, Pa., USA 1985).

As discussed above, a chemotherapy or endocrine therapy may involve, without limitation, administration of a chemotherapeutic agent or endocrine therapeutic agent comprising a small molecule, a peptide or a protein, an anthracycline, an alkylating agent, an alkyl sulfonate, an aziridine, an angiogenesis inhibitor, an ethylenimine, a methylmelamine, a nitrogen mustard, a nitrosourea, an antibiotic, an antimetabolite, a folic acid analogue, a purine analogue, a pyrimidine analogue, an enzyme, a podophyllotoxin, a platinum-containing agent or a cytokine in combination with N-2-pyridinyl-2-pyridinecarbothioamide or cambendazole. Thus, compositions comprising N-2-pyridinyl-2-pyridinecarbothioamide or cambendazole in combination with a chemotherapeutic agent or endocrine therapeutic agent selected from taxanes, tamoxifen, cisplatin, Adriamycin (ADR), 5-fluorouracil (5-FU), etoposide, doxorubicin, bevacizumab, HERCEPTIN (generic name, trastuzumab) or camptothecin. Exemplary angiogenesis inhibitors suitable for use as disclosed herein include, bevacizumab, VEGF-TRAP and variants thereof (see, for example, Proc. Natl. Acad. Sci., 2002, 99:11393-11398)), AdPEDF (Adenovector Pigment Epithelium-Derived Factor; Retina, The Journal Of Retinal And Vitreous Diseases, 2005, 25(No. 8):S48) small molecule tyrosine kinase inhibitors that target VEGFRs (such as cediranib (4-[(4-fluoro-2-methyl-1H-indol-5-yl)oxy]-6-methoxy-7-[3-(pyrrolidin-1-yl)propoxy]quinazoline), sunitinib (N-[2-(diethylamino)ethyl]-5-[(Z)-(5-fluoro-1,2-dihydro-2-oxo-3H-indol-3-ylidine)methyl]-2,4-dimethyl-1H-pyrrole-3-carboxamide), sorafenib (4-[4-[[4-chloro-3-(trifluoromethyl)phenyl]carbamoylamino]phenoxy]-N-methyl-pyridine-2-carboxamide) or pazopanib (benzenesulfonamide, 5-[4-[(2,3-dimethyl-2H-indazol-6-yl)methylamino]-2-amino]-2-methyl-monohydrochloride)), thalidomide (2-(2,6-dioxopiperidin-3-yl) isoindoline-1,3-dione) and lenalidomide (REVLIMID; 3-(4-amino-1-oxo-3H-isoindol-2-yl)piperidine-2,6-dione)).

Once inside, bacterial and parasitic pathogens often modulate their phagosome to establish an intracellular niche for survival and replication. Thus, another aspect of the invention provides methods for the treatment of pathogenic infections in an individual comprising the administration of N-2-pyridinyl-2-pyridinecarbothioamide or cambendazole alone or in combination with chemotherapeutic agents suitable for the treatment of the pathogenic infection. Non-limiting examples of pathogens suitable for treatment via the administration of compounds and compositions disclosed herein include the trypanosomes (e.g., T. cruzi, T. brucei, etc.), Brucella abortus, Legionella pneumophila and Porphyromonas gingivalis.

Thus, another aspect of the invention provides compositions comprising N-2-pyridinyl-2-pyridinecarbothioamide and/or cambendazole alone or in combination with a chemotherapeutic agent suitable for the treatment of the pathogenic infection (e.g., antibiotics). Non-limiting examples of antibiotics suitable for formulation with N-2-pyridinyl-2-pyridinecarbothioamide and/or cambendazole include tetracyclines, penicillins, melarsoprol, nifurtimox, pentamidine, eflornithine, macrolides (azithromycin), quinolones (ciprofloxacin, levofloxacin, moxifloxacin, gemifloxacin, trovofloxacin), doxycycline, minocycline, trimethoprim, sulfamethoxazole, erythromycin, benzylpenicillin, amoxicillin, ampicillin, ticarcillin piperacillin, cephalothin, cefuroxime, cefotaxime, cefoxitin, imipenem, cefamandole, cephaloridine, oleandomycin, metronidazole, spiramycin, or clindamycin.

Another aspect of the invention provides for a composition comprising a pharmaceutically acceptable diluent and N-2-pyridinyl-2-pyridinecarbothioamide and cambendazole. Such compositions can be used for the manufacture of a medicament for the treatment of any of the cancers or pathogenic conditions discussed herein.

A method of suppressing the lipidation of the Atg8 (also known as MAP-LC3 or LC3 for short) protein/polypeptide (autophagy-related protein 8 or microtubule associated protein light chain 3) comprising contacting a sample containing Atg8 (LC3) polypeptides with a compound selected from N-2-pyridinyl-2-pyridinecarbothioamide and/or cambendazole, or compositions thereof is also provided by the subject application. In these methods, the samples can be contacted in vitro. The subject invention also provides methods of inhibiting the lipidation of Atg8 polypeptides in vivo comprising the administration of a compound selected from N-2-pyridinyl-2-pyridinecarbothioamide and/or cambendazole, or compositions thereof to an individual. Cambendazole alone or compositions thereof, N-2-pyridinyl-2-pyridinecarbothioamide alone, or compositions thereof, or both N-2-pyridinyl-2-pyridinecarbothioamide and cambendazole, or compositions thereof can be used to contact the sample or for administration to an individual.

Additionally, a method of suppressing the expansion of an autophagosome (membrane-bound vacuole that sequesters cellular components and organelles destined for lysosomal degradation during autophagy) comprising contacting a cell with a compound selected from N-2-pyridinyl-2-pyridinecarbothioamide and/or cambendazole, or compositions thereof in an amount sufficient to suppress the expansion of an autophagosome. In this aspect of the invention, the contacting of the cell can be performed in vitro or in vivo. A compound selected from N-2-pyridinyl-2-pyridinecarbothioamide and/or cambendazole, or compositions thereof can be used to contact the cell in vitro or in an individual (in vivo). Cambendazole alone or compositions thereof, N-2-pyridinyl-2-pyridinecarbothioamide alone, or compositions thereof, or both N-2-pyridinyl-2-pyridinecarbothioamide and cambendazole, or compositions thereof can be used to contact the cell or for administration to an individual in order to suppress the expansion of an autophagosome.

All patents, patent applications, provisional applications, and publications referred to or cited herein are incorporated by reference in their entirety, including all figures and tables, to the extent they are not inconsistent with the explicit teachings of this specification. Following are examples which illustrate procedures for practicing the invention. These examples should not be construed as limiting. All percentages are by weight and all solvent mixture proportions are by volume unless otherwise noted.

Example 1

Identification of Compounds that Inhibit Atg4

Atg4 is a cysteine proteinase that cleaves the C-terminus of Atg8 (LC3) thereby enabling it to be conjugated to the lipid, phosphatidylethanolamine (PE). Atg8 is not essential for the formation of the autophagosome, but does affect the size of these vacuoles and their transport along microtubules. In silico molecular docking to select small compounds from the NCI database that would fit into this active site identified by spheres was performed (FIG. 1). The compounds were scored based on their potential to interact within the Atg4 pocket that contains histidine 280 and aspartic acid 278 and thus, inhibit the proteolytic activation and subsequent lipidation of Atg8 required for autophagy.

Example 2

Autophagy in Presence of Candidate Compounds

Figure 3:
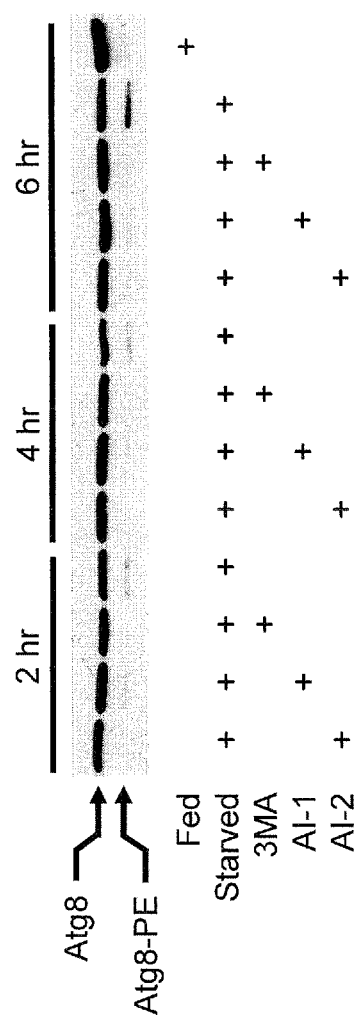
FIG. 3. Atg-4-targeted compounds suppress the lipidation of Atg8 (LC3) in Saos-2 osteosarcoma cells. The lipidation of Atg8 (Atg8-PE) was examined by Western blotting in fed and starved (medium lacking amino acids and serum) cells and in starved cells treated with 3-methyladenine (3MA), AI-1 and AI-2.
Figure 4:
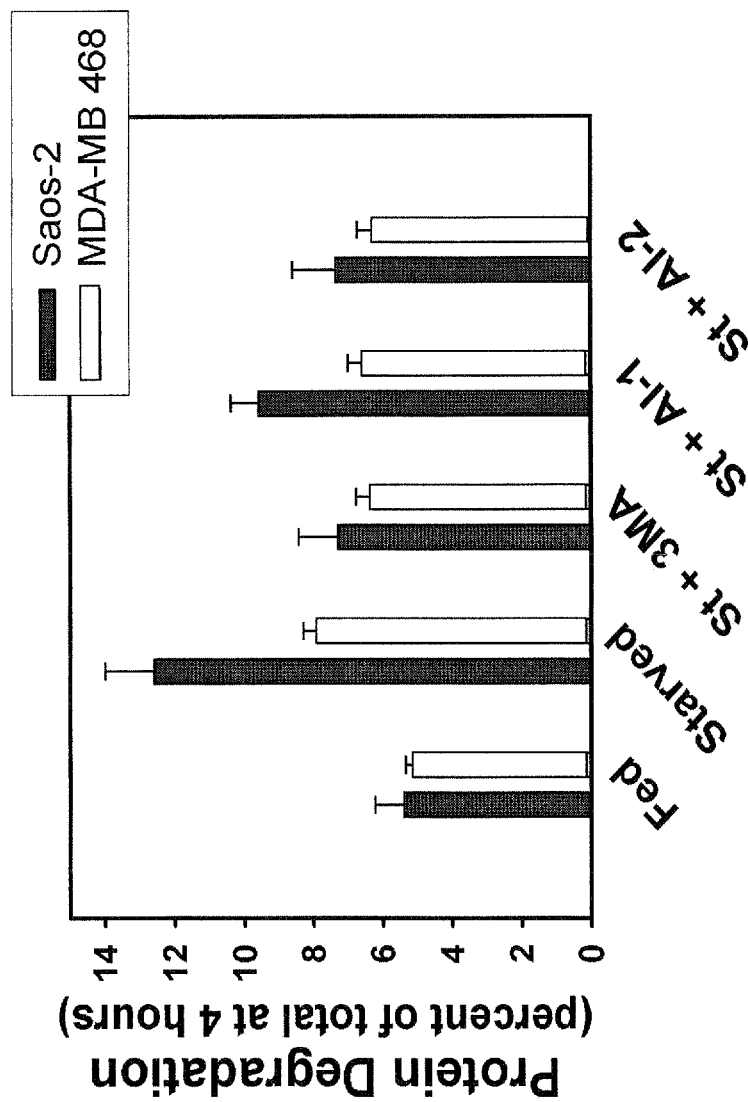
FIG. 4. Atg-4-targeted drugs suppress starvation induced (autophagy-mediated) protein degradation. Saos-2 and MDA-MB468 cells were incubated under nutrient fed and starved conditions in the presence and absence of 3-methyladenine (3MA), AI-1 and AI-2 and the rates of protein degradation measure by pulse-chase methodology with 14C-leucine. Bars=mean±SEM. n=4-6 trials.
Figure 5B:
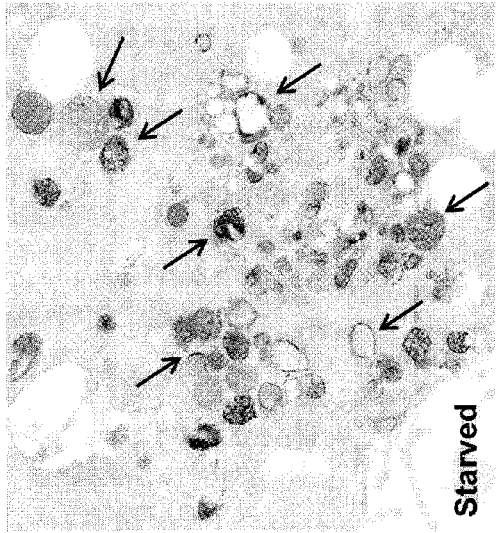
FIGS. 5A-5D. Atg-4-targeted drugs reduce the size of autophagic vacuoles. MDA-MB468 cells were incubated under nutrient fed (FIG. 5A) and starved (medium lacking amino acids and serum.
Figure 5A:
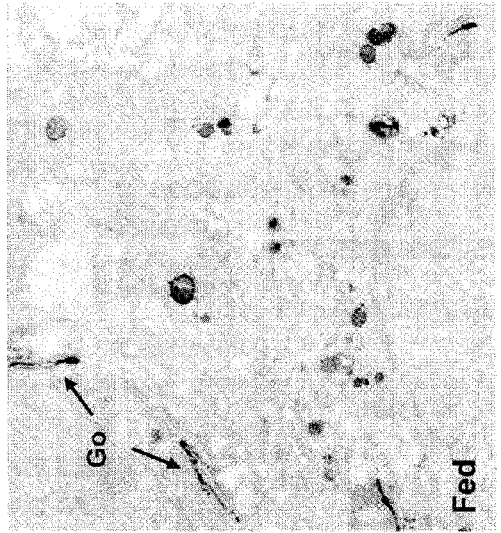
Figure 5D:
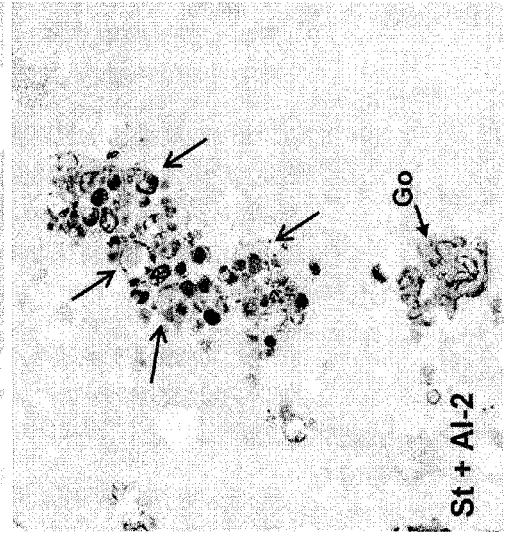
Figure 5C:
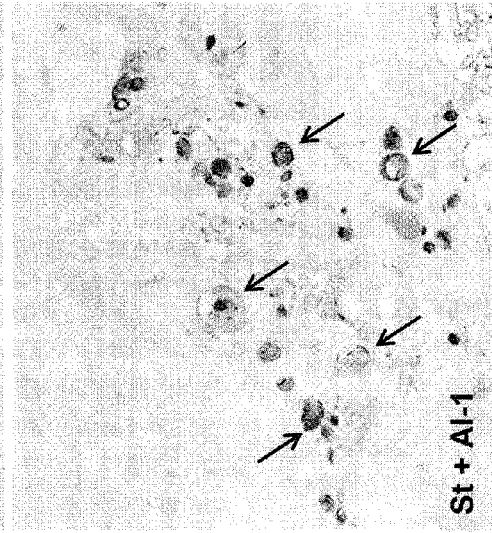

The Atg4 compounds were obtained from the National Cancer Institute (NCI) and then tested for their ability to suppress autophagy by observing the presence of autophagosomes in Saos-2 osteosarcoma and MDA-MB468 breast carcinoma cell lines stabling expressing Atg8 tagged with a green fluorescent protein (GFP-Atg8). Upon the onset of autophagy, Atg8 becomes lipidated being anchored to the autophagosome membrane whereby this protein then recruits additional membranes for expanding the size of the vacuoles and thus, regulating the degradative amplitude of autophagy. Of the more than twenty compounds tested that could fit into the Atg4 site, AI-1 and AI-2 were found to effectively inhibit the presence of GFP-Atg8 labeled autophagic vacuoles in nutrient-starved cell lines (FIG. 2). Compared to 70% of the starved cells containing autophagic vacuoles, less than 20% of those starved cells treated with AI-1 or AI-2 contained these vacuoles. These observations were consistent with the negative effects of these compounds on the lipidation of Atg8 (FIG. 3). Saos-2 cells expressing GFP-Atg8 were starved for amino acids for 2-6 h in the absence and presence of 3-methyladenine and the Atg4 compounds. The lipidated form of Atg8 (Atg8-PE) can be seen in nutrient-starved cells, but not in fed cells or starved cells treated with AI-1 or AI-2. The effects of AI-1 and AI-2 on the lipidation of Atg8 were coincident with a reduction in the degradation of endogenous proteins (FIG. 4) and a decrease in the size of those autophagic vacuoles present (FIGS. 5C and 5D). When MDA-MB468 cells are incubated in medium lacking amino acids and serum, we observe a dramatic increase in autophagosomes (lacking CMPase) and autolysosomes (autophagic vacuoles containing the lysosomal marker, CMPase). However, when we treated these starved cells with AI-1 or AI-2, the autophagic vacuoles were smaller in size. In fact, the autophagic vacuoles in drug treated cells were on average over 50% smaller than untreated. We also noticed a dramatic redistribution of the autophagic vacuoles to a centralized region of the cell when treated with AI-2 (FIG. 5I)). These compounds, by altering the lipidation of Atg8 (LC3), not only reduced the size of the autophagic vacuoles, but also affected their movements along the microtubules. In summary, these results demonstrate that AI-1 and AI-2 suppress the amplitude of autophagy by inhibiting the lipidation of Atg8 (LC3).

Figure 6B:
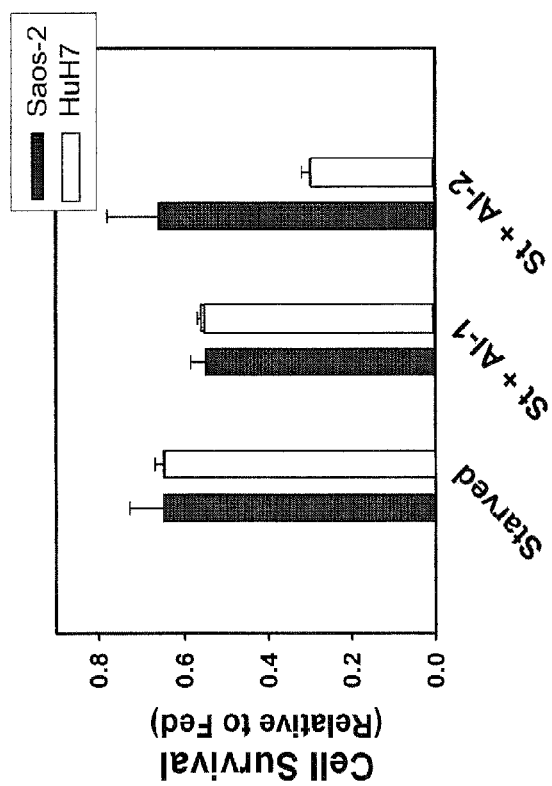
FIGS. 6A-B. Atg-4-targeted drugs decrease cell survival of nutrient deprived cancer cells. Control breast epithelial MCF10A, MDA-MB 468 breast carcinoma, Saos2 osteosarcoma, and HuH7 hepatoma were incubated under nutrient fed and starved conditions in the presence and absence of AI-1 and AI-2. The number of viable cells on the plate relative to fed after 24 hrs was quantified by crystal violet staining. Bars=mean±SEM, n=4-6 trials.
Figure 6A:
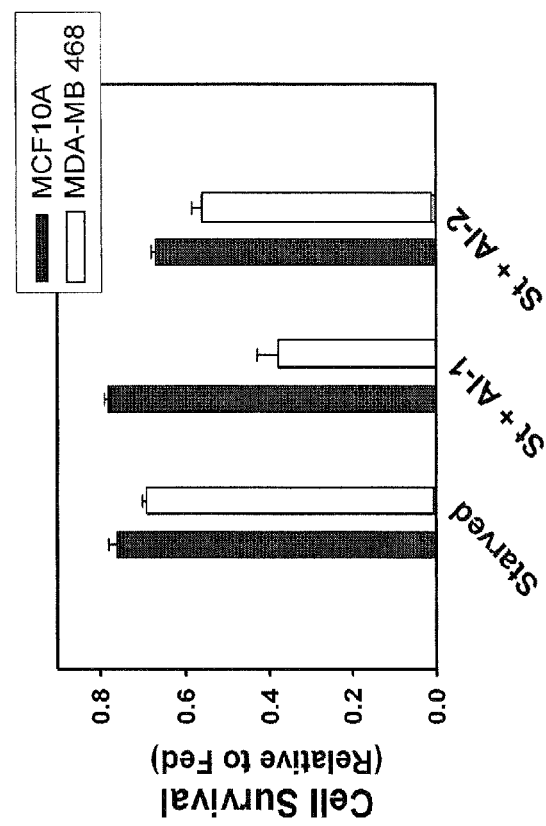

Atg-4-Targeted Compounds Suppress Cancer Cell Survival:

During the early stages of tumor growth prior to vascularization, cancer cells are exposed to conditions lacking nutrients and growth factors. These cells are able to survive these conditions by activating autophagy, thereby degrading endogenous macromolecules and recycling the nutrients. In order to simulate these conditions in vitro, we have incubated cells in the absence of amino acids and serum. Approximately 65-75% of the normal and cancer cell lines tested survived when exposed to nutrient-deprived serum-free medium for 24 hours. The survival of nutrient-starved normal breast epithelial cells (MCF10A) was only moderately affected by AI-1 and AI-2. However, the survival of nutrient-starved breast carcinoma MDA-MB468 cells was dramatically reduced to less than 40% when treated with AI-1 (FIG. 6A). Meanwhile, AI-2 effectively decreased the survival of nutrient starved HuH7 hepatoma cells to 30% of controls. AI-1 had moderate activity on the survival of Saos-2 and HuH7 cells (FIG. 6B). In conclusion, these findings imply that AI-1 and AI-2 can repress the survival of nutrient-deprived breast carcinoma, osteosarcoma, and hepatoma cells.

Atg-4-Targeted Compounds Repress the Intracellular Survival of Pathogens:

We have previously shown that autophagy is required for *P. gingivalis* to thrive within host endothelial cells (Dorn, B. R., Dunn, W. A., Jr., and Progulske-Fox, A. "*Porphyromonas gingivalis* traffics to autophagosomes in human coronary artery endothelial cells" *Infect Immun*, 2001, Vol. 69, pp. 5698-5708). In fact, in the absence of autophagy, this bacterium fails to form a "replicative vacuole" and is instead transported to lysosomes where the bacterium is destroyed by digestive enzymes. We then tested the efficacy of AI-1 and AI-2 to promote the intracellular movements of this intracellular pathogen to the destructive lysosomes. We found that *P. gingivalis* survived within the "replicative vacuole" in untreated endothelial cells (FIG. 7A). In cells treated with the autophagy inhibitor, 3-methyladenine (3MA), partially degraded bacteria were found in CMPase-positive lysosomes (FIG. 7B). In the presence of AI-1 or AI-2, the bacteria in various degraded states were observed in CMPase-positive lysosomes (FIGS. 7C and 7D). In summary, these results suggest that AI-1 and AI-2 effectively suppressed autophagy, thereby resulting in the destruction of the intracellular pathogen, P. gingivalis, and host cell survival.

It should be understood that the examples and embodiments described herein are for illustrative purposes only and that various modifications or changes in light thereof will be suggested to persons skilled in the art and are to be included within the spirit and purview of this application. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

We claim:

1. A method of increasing an individual's responsiveness to a cancer therapy comprising inhibiting Atg4 function in a cell currently undergoing the cancer therapy, said method comprising the administration of a composition comprising:
   a) N-2-pyridinyl-2-pyridinecarbothioamide, or
   b) N-2-pyridinyl-2-pyridinecarbothioamide and cambendazole;
   to an individual having solid tumor, said composition being administered alone or in combination with a chemotherapeutic agent.

2. A method of increasing an individual's responsiveness to a cancer therapy comprising inhibiting Atg4 function in a cell currently undergoing the cancer therapy, said method comprising the administration of a composition comprising:
   a) N-2-pyridinyl-2-pyridinecarbothioamide, or
   b) N-2-pyridinyl-2-pyridinecarbothioamide and cambendazole;
   to an individual having lung cancer, said composition being administered alone or in combination with a chemotherapeutic agent.

3. The method according to claim 2, wherein said composition comprises N-2-pyridinyl-2-pyridinecarbothioamide and is administered in combination with a chemotherapeutic agent to an individual having lung cancer.

4. The method according to claim 2, wherein said composition comprises N-2-pyridinyl-2-pyridinecarbothioamide and cambendazole and is administered in combination with a chemotherapeutic agent to an individual having lung cancer.

5. The method according to claim 2, wherein said composition comprising N-2-pyridinyl-2-pyridinecarbothioamide is administered to an individual having lung cancer.

6. The method according to claim 2, wherein a composition comprising N-2-pyridinyl-2-pyridinecarbothioamide and cambendazole is administered to an individual having lung cancer.

7. A method of treating cancer comprising administering an effective amount of a composition comprising:
   a) N-2-pyridinyl-2-pyridinecarbothioamide, or
   b) N-2-pyridinyl-2-pyridinecarbothioamide and cambendazole;
   to an individual having a solid tumor, said composition being administered alone or in combination with a chemotherapeutic agent.

8. The method according to claim 7, wherein said composition comprises N-2-pyridinyl-2-pyridinecarbothioamide and is administered in combination with a chemotherapeutic agent to an individual having a solid tumor.

9. The method according to claim 7, wherein said composition comprises N-2-pyridinyl-2-pyridinecarbothioamide and cambendazole and is administered in combination with a chemotherapeutic agent to an individual having a solid tumor.

10. The method according to claim 7, wherein said composition comprising N-2-pyridinyl-2-pyridinecarbothioamide is administered to an individual having a solid tumor.

11. The method according to claim 7, wherein a composition comprising N-2-pyridinyl-2-pyridinecarbothioamide and cambendazole is administered to an individual having a solid tumor.

12. A method of treating lung cancer comprising administering an effective amount of a composition comprising:
   a) N-2-pyridinyl-2-pyridinecarbothioamide, or
   b) N-2-pyridinyl-2-pyridinecarbothioamide and cambendazole;
   to an individual having lung cancer, said composition being administered alone or in combination with a chemotherapeutic agent.

13. The method according to claim 12, wherein said composition comprises N-2-pyridinyl-2-pyridinecarbothioamide and is administered in combination with a chemotherapeutic agent to an individual having lung cancer.

14. The method according to claim 12, wherein said composition comprises N-2-pyridinyl-2-pyridinecarbothioamide and cambendazole and is administered in combination with a chemotherapeutic agent to an individual having lung cancer.

15. The method according to claim 12, wherein said composition comprising N-2-pyridinyl-2-pyridinecarbothioamide is administered to an individual having lung cancer.

16. The method according to claim 12, wherein said composition comprising N-2-pyridinyl-2-pyridinecarbothioamide and cambendazole is administered to an individual having lung cancer.

* * * * *

UNITED STATES PATENT AND TRADEMARK OFFICE
CERTIFICATE OF CORRECTION

PATENT NO. : 8,545,841 B2
APPLICATION NO. : 12/811646
DATED : October 1, 2013
INVENTOR(S) : William A. Dunn et al.

It is certified that error appears in the above-identified patent and that said Letters Patent is hereby corrected as shown below:

In the Specification

Column 5,
Line 40, "(benzenesulfonamide,5-[4-[(2,3-dimethyl-2H-indazol-6-yl)methylamino]-2-amino]-2-methyl-monohydrochloride))" should read --(benzenesulfonamide,5-[4-[(2,3-dimethyl-2H-indazol-6-yl)methylamino]-2-pyrimidinyl]-amino]-2-methyl-monohydrochloride))--.

Column 7,
Line 46, "(FIG. 51))" should read --(FIG. 5D)--.

Signed and Sealed this
Twentieth Day of May, 2014

Michelle K. Lee
*Deputy Director of the United States Patent and Trademark Office*